United States Patent [19]

Nohso

[11] Patent Number: 4,518,264
[45] Date of Patent: May 21, 1985

[54] STIRRING APPARATUS

[75] Inventor: Hidenori Nohso, Kakogawa, Japan

[73] Assignee: Mitsubishi Kasei Kogyo Kabushiki Kaisha, Tokyo, Japan

[21] Appl. No.: 511,947

[22] Filed: Jul. 8, 1983

[30] Foreign Application Priority Data

Jul. 13, 1982 [JP] Japan ................................ 57-120596
Aug. 18, 1982 [JP] Japan ................................ 57-142163

[51] Int. Cl.³ .............................................. B01F 9/00
[52] U.S. Cl. ..................................... 366/208; 422/63; 422/65; 422/99
[58] Field of Search ............... 366/202, 208, 209, 210, 366/211, 215, 216, 219, 237, 602; 494/20; 422/63, 65, 72, 99, 104

[56] References Cited

U.S. PATENT DOCUMENTS

| | | | |
|---|---|---|---|
| 3,679,129 | 7/1972 | Livshitz et al. | 422/72 X |
| 3,883,306 | 5/1975 | Widen | 422/65 X |
| 4,373,029 | 2/1983 | Nees | 366/219 X |
| 4,456,580 | 6/1984 | Yamada et al. | 422/63 |

Primary Examiner—Philip R. Coe
Attorney, Agent, or Firm—Oblon, Fisher, Spivak, McClelland and Maier

[57] ABSTRACT

A number of test tubes containing blood to be diagnosed are arranged in a matrix in a magazine. The test tubes of the foremost row are sent out one after one to a sample holding and transfer apparatus which transfers the sample to a stirring apparatus where the test tube is swung and alternately rotated in opposite directions by a pair of rollers. The stirred test tube is sent to blood diagnostic apparatus and then sent back to the rearmost row of the matrix. When all tubes in the foremost row are sent out, the remaining rows are moved to sequentially send out the test tubes in the second row.

10 Claims, 16 Drawing Figures

STIRRING APPARATUS

BACKGROUND OF THE INVENTION

This invention relates to stirring apparatus, and more particularly apparatus for stirring blood contained in a test tube to a homogeneously suspended state when supplying the blood in the test tube to an automatic diagnostic apparatus, and automatic sample supply apparatus which sequentially supply to and return from the diagnostic apparatus a plurality of test tubes arranged in a predetermined pattern, for example a matrix, in a magazine.

Blood diagnostic apparatus has been known capable of measuring with high reproduceability and at a high accuracy the number of red blood-corpuscles, the number of white blood-corpuscles, the number of blood plasmas, the concentration of coloring matter of the red blood-corpuscles, hematocrit value, etc., by utilizing a combination of laser technique and computer technique. When diagnosing blood with such diagnostic apparatus, a test tube containing sampled blood is brought to a test tube set position where the blood in the test tube is sucked by an aspirator extending from the diagnostic apparatus and supplied to a measuring unit thereof.

When supplying the blood to be diagnosed to the diagnostic apparatus, it is necessary to maintain the blood in a homogeneously suspended state. According to the prior art practice, the operator stirres the blood by shaking the bottom of the test tube with his hand. With manual stirring, however, stirred state differs greatly for respective test tubes, thus failing to uniformly stir so that it requires a considerable skill to obtain satisfactorily suspended state by stirring without destroying red and white blood corpuscles. Except a case wherein blood should be rapidly diagnosed, in a hospital or the like where blood of many patients are to be diagnosed, it is necessary to diagnose several hundreds or more samples, which requires not only many operators but also large labor and time.

Except an urgent case, where several hundreds of sample blood are to be diagnosed, with a prior art machine, the operator brings the test tubes, one after the other, to the test tube set position of the diagnostic apparatus, then slightly elevates the tube at the set position to insert the aspirator into the tube, finally bring back the empty tube. This cycle of operation is repeated for a number of the test tubes.

In some cases, the blood in the test tube is not completely sucked and the test tube containing remaining blood is transferred to other apparatus where different type of diagnosis is made. Where a number of test tubes are used it is advantageous to array them in rows and columns of a matrix. In such a case, it is necessary to bring back the test tube containing remaining blood to the original position of the matrix which also increases the burden of the operator.

SUMMARY OF THE INVENTION

Accordingly, it is an object of this invention to provide a novel apparatus for efficiently stirring a liquid sample contained in a test tube for obtaining a homogeneously suspended state.

Another object of this invention is to provide an automatic test tube feeding device which sends out test tubes one after one from a storage magazine storing a number of test tubes in aligned rows and columns, feeds the sent out test tube to a diagnostic apparatus after stirring and then returns the test tube from the apparatus to the original position in the storage magazine.

According to one aspect of this invention there is provided stirring apparatus comprising a holder for supporting a test tube containing a sample to be rotatable about the longitudinal axis of the test tube, means for swingably supporting the holder, and means for swinging the test tube while rotating the same in forward and reverse directions.

According to another aspect of this invention there is provided automatic feed apparatus comprising a magazine in which a plurality of samples, each having a test tube containing a sample and a holder for holding the test tube, are aligned in a matrix of a plurality of rows and a plurality of columns; a send out device for intermittently moving the samples of the foremost row by a distance corresponding to one sample; sample holding and transfer means for receiving one sample sent out from the magazine; means for reciprocating the sample holding and transfer means toward and away from stirring apparatus for returning the samples from the sample holding and transfer means back to the rearmost row in the magazine, and means for moving all rows remaining in the magazine toward the foremost row by a distance corresponding to the width of one row when all samples of the foremost row have been sent out of the magazine.

DESCRIPTION OF THE PREFERRED EMBODIMENTS

Figure 1:
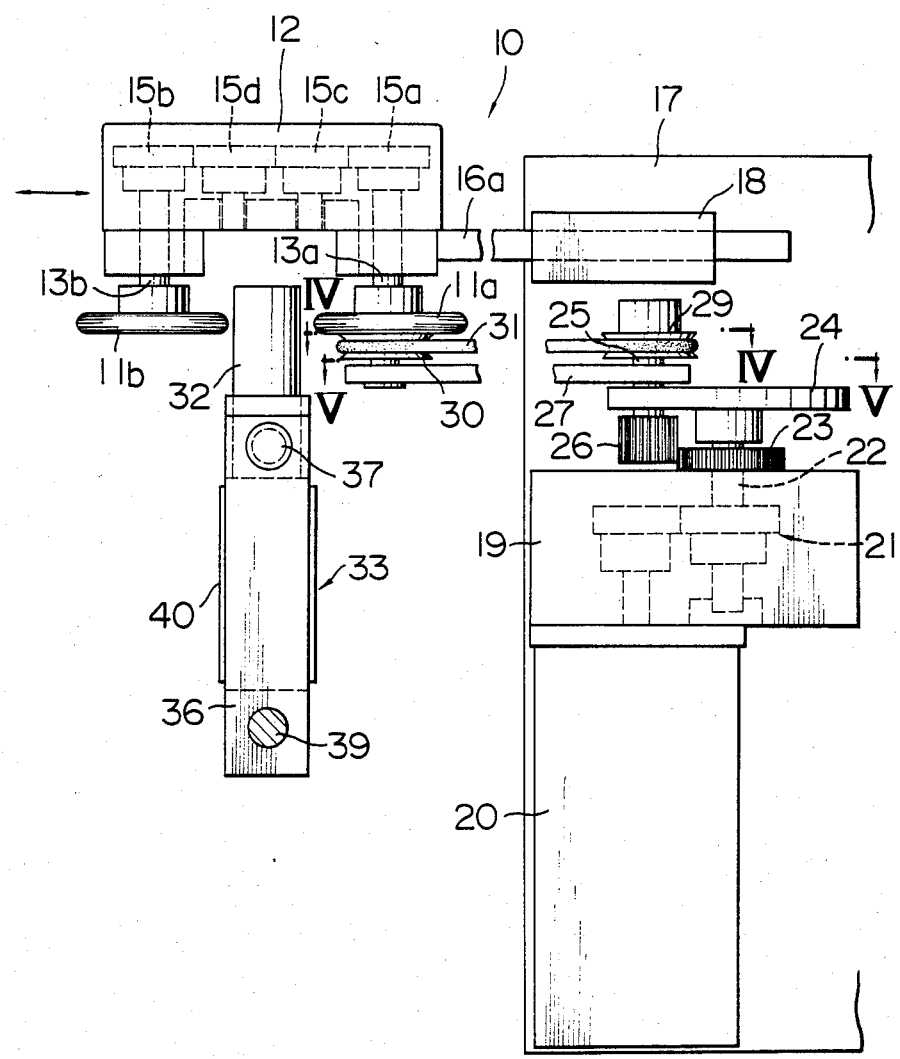
FIG. 1 is a front view showing one embodiment of the stirring apparatus according to this invention.
Figure 2:
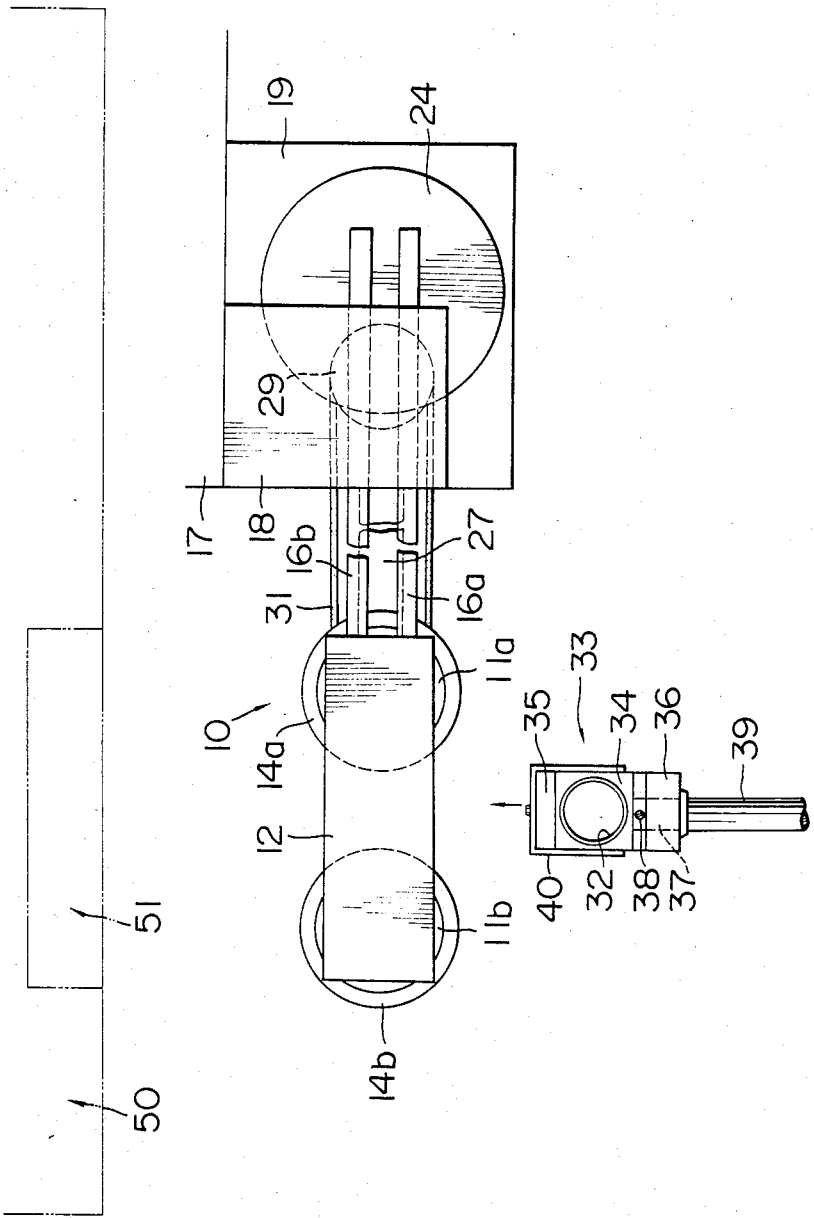
FIG. 2 is a plan view of the stirring apparatus shown in FIG. 1.
Figure 3:
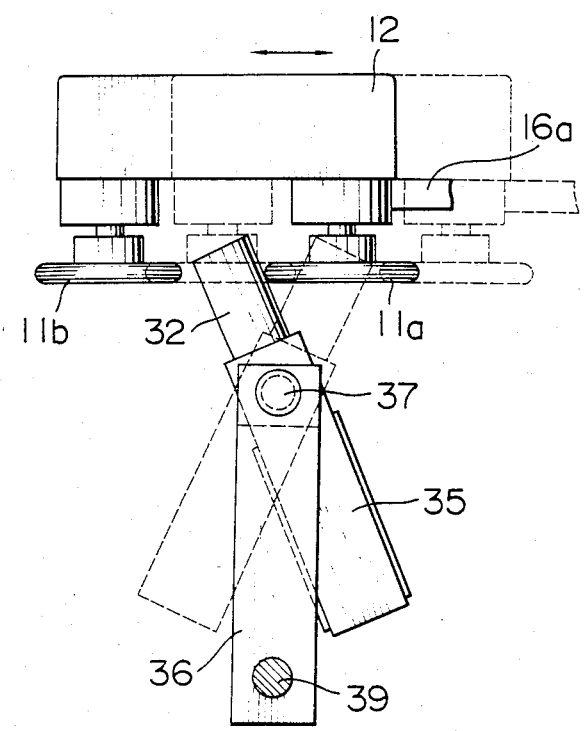
FIG. 3 is a fragmental front view for explaining the operation of the apparatus shown in FIG. 1.

A preferred embodiment of the stirring apparatus of this invention shown in FIGS. 1, 2 and 3 will firstly be described. As shown, the stirring apparatus 10 comprises two spaced rollers 11a and 11b disposed in the same plane, and a supporting unit 12 rotatably supporting these rollers. The roller supporting unit 12 (hereinafter merely called a unit) supports two parallel and vertically extending shafts 13a and 13b, and rollers 11a and 11b provided with rubber rings 14a and 14b are secured to the lower ends of the shafts 13a and 13b projecting from the lower surface of the unit 12. To the upper ends of the shafts 13a and 13b are secured gears 15a and 15b which are coupled together through idle gears 15c and 15d so that when one of the rollers 11a is rotated, the other roller 11b is rotated in the opposite direction. The gear 15a–15d are housed in the unit 12.

A pair of parallel guide rods 16a and 16b are secured to one side of the unit 12 to extend outwardly. The guide rods 16a and 16b are slidably received in openings of a supporting member 18 projecting from a stationary wall 17 of the stirring apparatus. Thus, the unit 12 with two rollers 11a and 11b is supported to be movable in the direction of alignment of these rollers.

Figure 4:
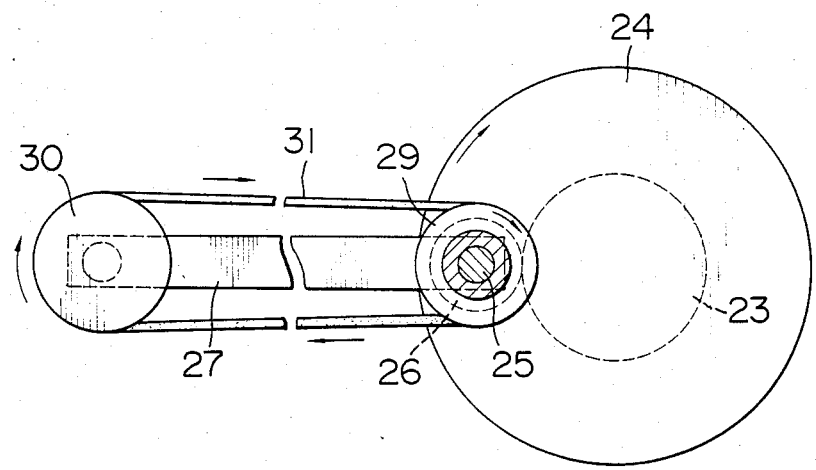
FIGS. 4 and 5 are sectional views respectively taken along lines IV—IV and V—V in FIG. 1.
Figure 5:
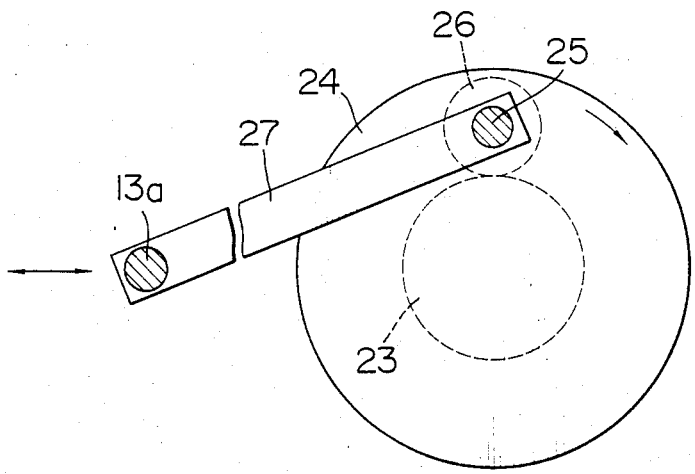

A gear box 19 secured to the stationary supporting member 17 is disposed beneath the supporting member 18 that slidably supports the unit 12 and a source of drive, e.g. an electric motor 20 is secured to the lower surface of the gear box 19. An output shaft 22 of a reduction gear train 21 contained in the gear box 19 loosely extends upwardly through the center opening of a spur gear 23 secured to the upper surface of the gear box 19 and a circular disc 24 is secured to the upper end of the shaft 22. A stub shaft 25 is rotatably supported by the disc at an eccentric position with respect to its axis and a gear 26 meshing with the stationary spur gear 23 is secured to the lower end of the stub shaft 25. One end of an operating lever 27 is freely fitted on the upper end of the stub shaft 25 and a pulley 29 is also secured to the upper end. A pulley 30 is coaxially secured to the shaft 13a beneath the roller 11a, and the other end of the operating lever 27 is freely fitted to the lower end of the shaft 13a. The rotation of the pulley 29 is transmitted to the pulley 30 through a rubber belt 31. The construction described above is clearly shown in FIGS. 4 and 5.

Figure 6:
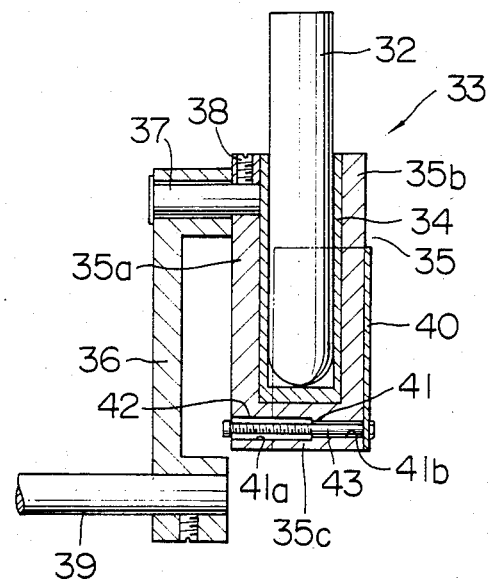
FIG. 6 is a longitudinal sectional view showing a device that swingably supports a test tube.
Figure 7:
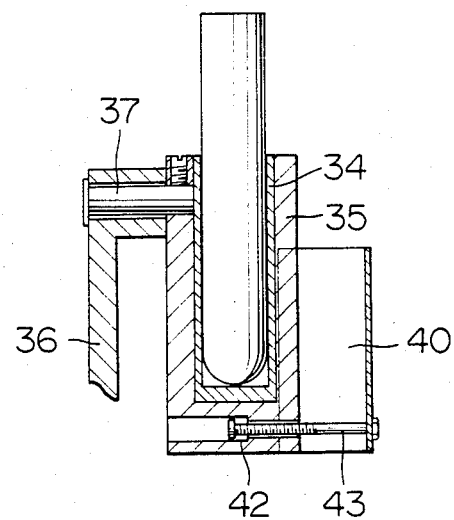
FIG. 7 is view similar to FIG. 6 with a protective cover opened.

In a space between two rollers 11a and 11b is disposed a test tube 32 rotatably and swingably supported by a device 33, the detail thereof being shown in FIGS. 6 and 7. As shown in FIG. 6, the lower end of the test tube 32 is received in an opening of a holder 34, the diameter of the opening being slightly larger than the outer diameter of the test tube so that it is rotatable about the axis of the holder 34. It is advantageous to form the holder 34 with a substance having a small coefficient of friction, for example, Duracome resin (trade name) for the purpose of decreasing as far as possible, the friction against the rotation of the test tube.

The cylindrical holder 34 is accommodated in a holder support 35 including a pair of opposing side walls 35a and 35b and a bottom wall 35c and having a U-shaped cross-sectional configuration. A laterally projecting pin 37 is secured to the upper end of the holder support 35 by a set screw 38 at a position a little higher than one half of the length of the test tube 32 accommodated in the holder 34. The pin 37 is rotatably supported by a supporting member 36 and is prevented from being withdrawn by a flange at the outer end of the pin 37. Accordingly, the holder support 35 can swing about pin 37. The lower end of the supporting member 36 is secured to the supporting rod 39.

A letter U shaped protective cover 40 is provided for the holder support 35 to open and close a pair of side openings thereof. Since the purpose of the protective cover 40 is to prevent the holder 34 from dropping out of the holder support 35, its height may be a little larger than one half of the height of the holder support 35, and the protective cover 40 is slidably connected to the bottom of the holder support 35. More particularly, a horizontal slot 41 formed in the bottom portion 35c of the holder support 35 comprises an enlarged diameter portion 41a of a predetermined length and a small diameter portion 41b. A coil spring 42 is inserted into the enlarged diameter portion 41a to surround a connecting rod 43 inserted into the slot 41. The outer end of the connecting rod 43 is secured to the side wall of the protective cover 40 facing the side wall 35b of the holder support 35, whereas the inner end is provided with an enlarged head for compressing the spring 42. Accordingly, by the force of the spring 42, the protective cover 40 is normally held at a position shown in FIG. 6 for closing the side openings of the holder support 35. When the protective cover 40 is moved to a position shown in FIG. 7 the side openings of the holder support 35 are opened.

The stirring apparatus described above operates as follows.

At first, the test tube 32 containing sampled blood is received in the holder 34 and then the holder 34 is received in the holder support 35 through a side opening thereof opened by moving the protective cover 40 to the position shown in FIG. 7. Then by advancing the supporting rod 39 the top portion of the test tube 32 is brought to a position between two rollers 11a and 11b as shown in FIG. 1.

Thereafter, the motor 20 is started to rotate disc 24 through the speed reduction gear train 21 and shaft 22. As the disc 24 is rotated, the eccentric shaft 25 revolves about the axis of disc 24 to rotate gear 26 meshing with the stationary gear 23, whereby the gear 26 rotates about the axis of shaft 25. Consequently, the slidable unit 12 is reciprocated by the crank motion of operating lever 27 caused by the revolution of gear 26. At the same time, the rotation of shaft 25 is transmitted to roller 11a through pulleys 29 and 30 and rubber belt 31, and the rotation of roller 11a is transmitted to another roller 11b through gears 15a–15d in the unit 12 to rotate the roller 11b in the opposite direction.

In this manner, two rollers 11a and 11b are reciprocated in the direction of their alignment while being rotated in the opposite direction. Consequently, the test tube 32 with its head positioned between rollers 11a and 11b is swung about pin 37 together with holder 34 and the holder support 35. When both sides of the top end of the test tube 32 are alternately engaged by the rollers 11a and 11b, it is rotated in the holder 34 by the frictional engagement with the rollers. As above described, since rollers 11a and 11b are rotated in the opposite directions, the direction of rotation of the test tube reverses as the rollers come into contact with the test tube change. Thus, the direction of rotation of the test tube 32 alternately reverses while swinging. Since the pin 37 about which the test tube 32 is swung is positioned at a position somewhat higher than the center of the length of the test tube 32, the bottom thereof is swung much more than the top. As a consequence, the blood in the test tube is throughly stirred without destroying red and white blood-corpuscles and there is no difference between the suspended states of respective test tubes.

When the stirring has been made for a predetermined interval, the test tube is brought back to the position shown in FIG. 1 and the device 33 swingably supporting the test tube is advanced beneath the unit 12 to the test position 51 of the blood diagnostic apparatus 50 (see FIG. 2) by the foreward movement of the supporting rod 39. Then the aspirator (not shown) of the blood diagnostic apparatus 50 is inserted into the test tube to suck all or a portion of the sample blood to perform various tests.

Figure 8:
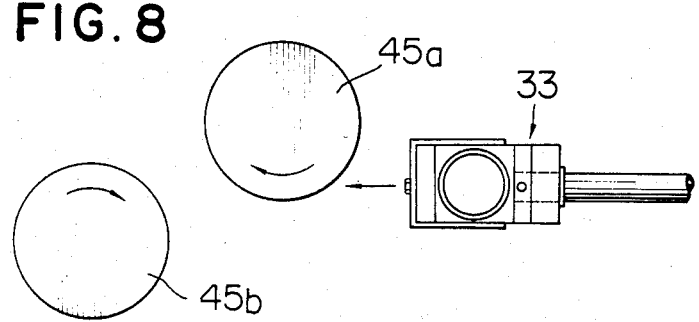
FIG. 8 is a plan view diagrammatically showing the relation between two rollers and a device for swingably supporting a test tube utilized in a modified embodiment of this invention.

Although in the foregoing embodiment the unit 12 is reciprocated in the direction of alignment of two rollers 11a and 11b for swinging the test tube, it should be understood that the invention is not limited to such specific construction. For example, as a modification shown in FIG. 8, at least two rollers 45a and 45b rotating in the opposite directions can be positioned in a staggered relation with respect to the direction of movement of the device so as to bring the test tube into contact alternately with rollers 45a and 45b.

Figure 9:
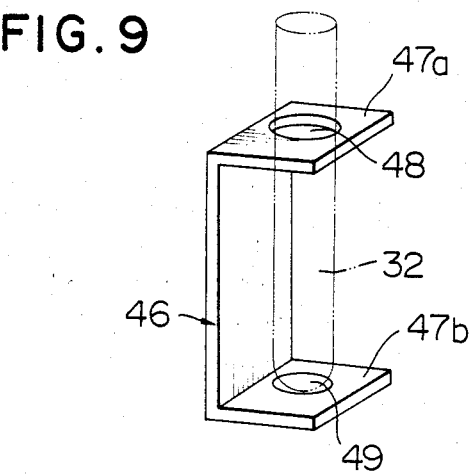
FIG. 9 is a perspective view showing a modified holder.

Furthermore, instead of using a hollow cylindrical holder 34, a U shaped holder 46 as shown in FIG. 9 can be used. The upper leg 47a of the holder 46 is provided with an opening 48 for receiving the test tube, whereas the lower leg 47b is formed with a circular recess 49 for receiving the bottom of the test tube. This holder decreases the contact area between it and the test tube so that the test tube can be rotated smoothly.

Figure 10:
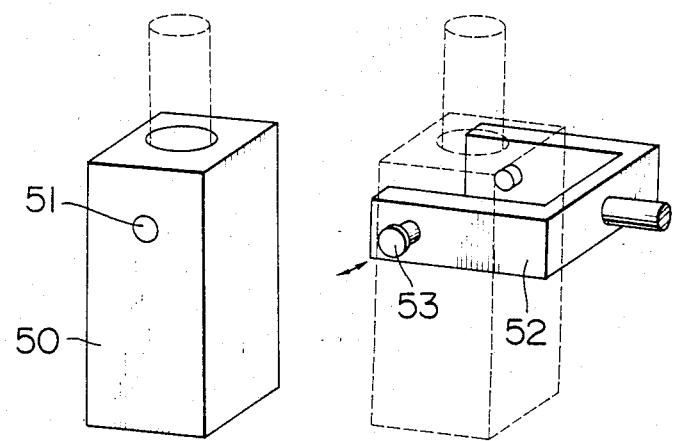
FIG. 10 is a perspective view showing another example of a holder and a holding member.

According to a further modification shown in FIG. 10, recesses 51 are formed on the opposite side surfaces of a holder 50 for receiving connecting pins 53 of a holder sopport 52.

Where the stirring apparatus described above is used, since uniform and rapid stirring can be made automatically, many test tubes can be manipulated in a short time and with lesser labor. Moreover, homogeneously suspended state of the sampled blood can be obtained for all test tubes regardless of the number thereof.

Figure 11:
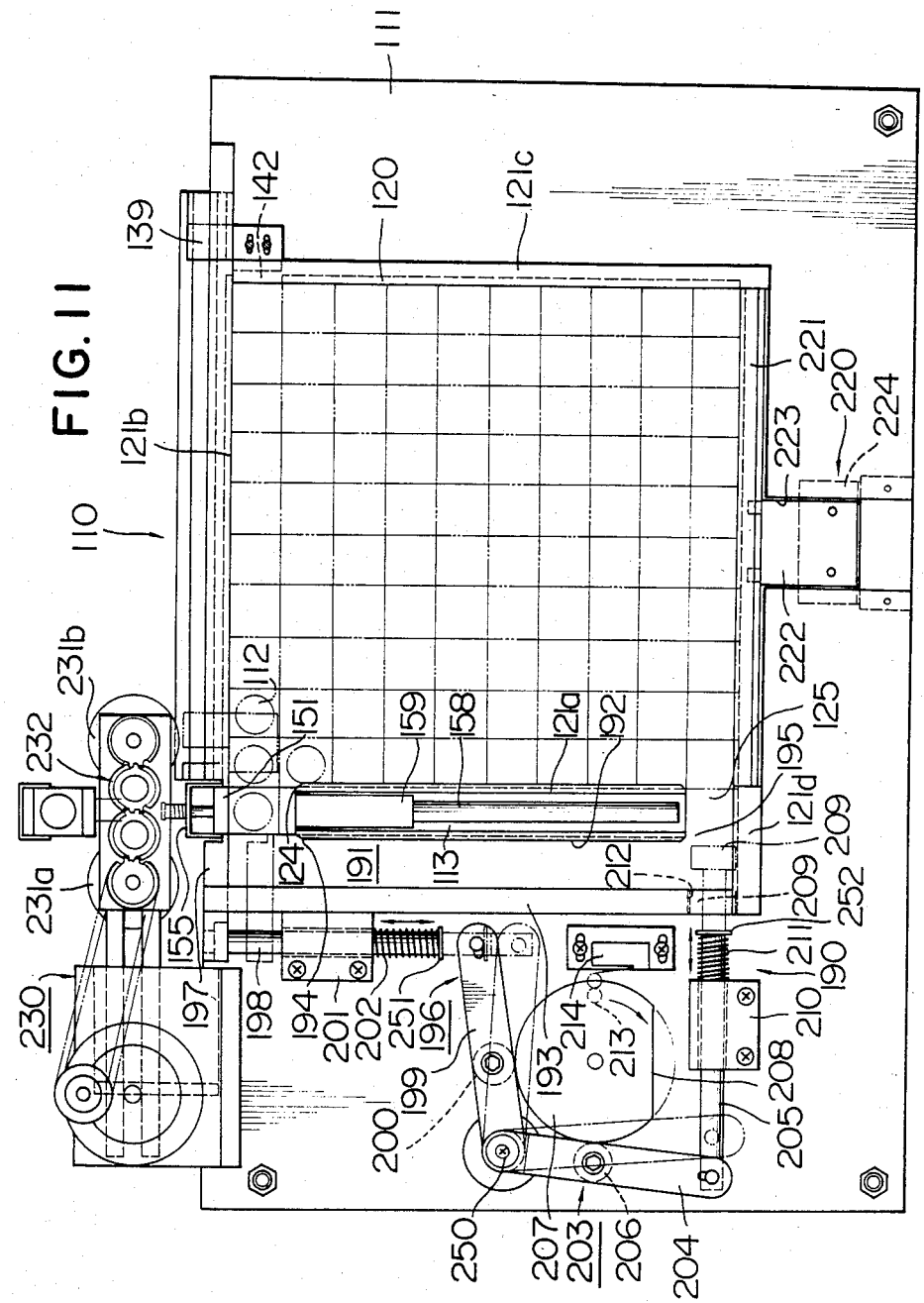
FIG. 11 is a plan view showing one example of automatic sample feeding apparatus utilized in this invention.

An automatic sample feed apparatus 110 which sequentially feeds and removes a number of test tubes containing sampled blood to and from an automatic diagnostic apparatus will be described with reference to FIGS. 11 through 15. In this example, it is assumed that 100 test tubes are used. A term sample is used herein to mean a test tube and a holder thereof regardless of whether the test tube contains blood or other liquid sample to be diagnosed or not. The principal elements of the automatic sample feed apparatus 110 are a storage magazine 120 mounted on a supporting plate 111, a send out device 130, a sample holding and transfer device 150 and a feed device 190. The detail of these elements is as follows. More particularly, four side plates 121a-121d are mounted on the supporting plate 111 to define the square magazine 120 in which 100 samples 112 are arranged in a matrix including 10 columns and 10 rows, each containing 10 samples 112. Samples 112 in the uppermost row are intermittently shifted to the left by the send out device 130 by a distance corresponding to one sample 112. Since FIG. 11 is a plan view its upper side is a fore or front side, but for the sake of description fore side is called uppermost side as viewed in FIG. 11.

Figure 12:
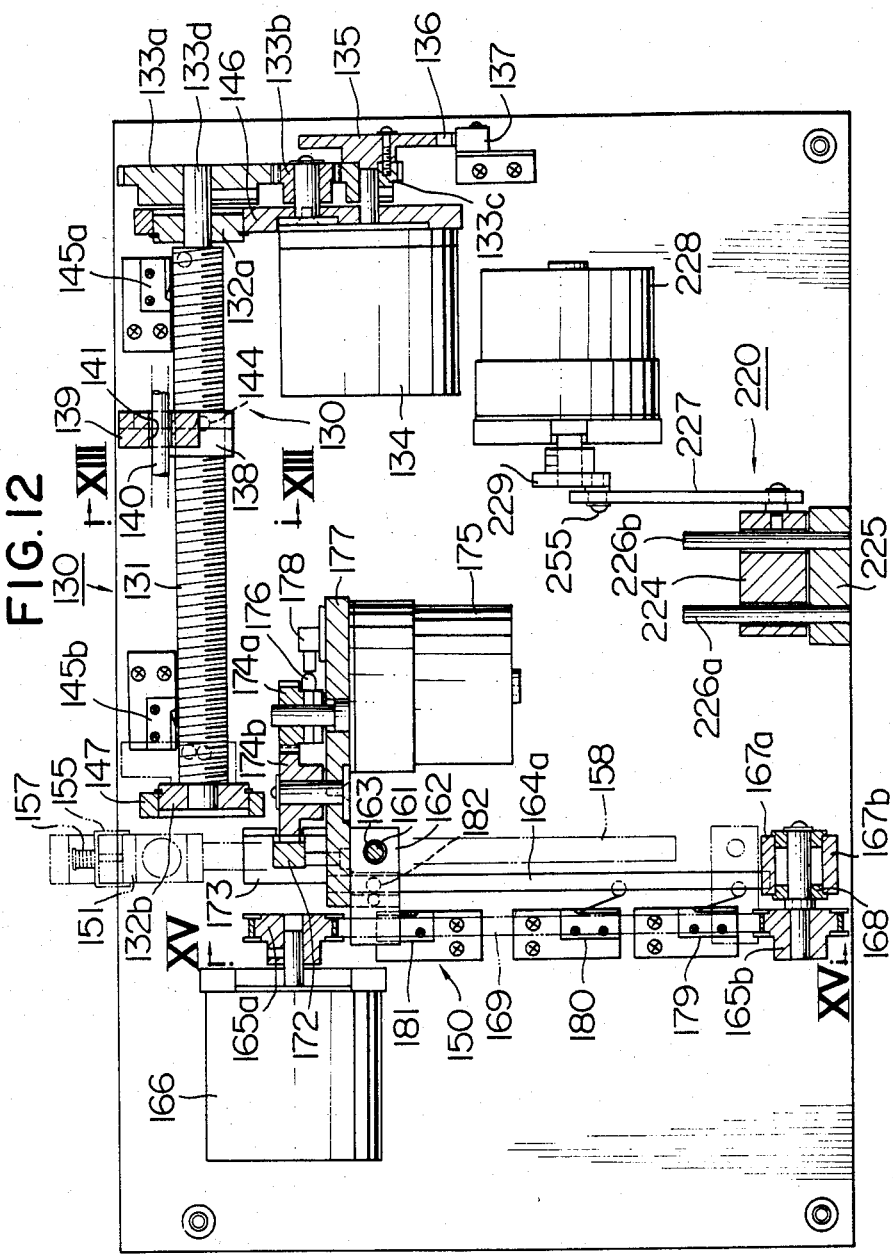
FIG. 12 is a bottom plan view showing the interior of the automatic sample feeding apparatus with the bottom plate removed.

Most elements of the send out device 130 are contained in a box connected to the lower side of the supporting plate 111. More particularly, as shown in FIG. 12 the send out device 130 comprises a feed screw 131 along the uppermost row of the samples, the opposite ends of the feed screw 131 being rotatably supported by bearings 132a and 132b. A gear 133a is secured to a spindle 133d connected to the righthand end of the feed screw 131 and extending through the bearing 132a, and the gear 133a is driven by an electric motor 134 or other drive source, through a gear 133c and an intermediate idle gear 133b. A disc 135 is coaxially secured to one side of the gear 133c, the disc 135 being provided with a projection 136 on its periphery for actuating a limit switch 137 which is opened when engaged by the projection 136. Accordingly, when the gear 133a is rotated one revolution by the motor 134, the limit switch 137 deenergizes the motor 134 so that the feed screw 131 is rotated by an amount determined by one rotation of the gear 133c.

Figure 13:
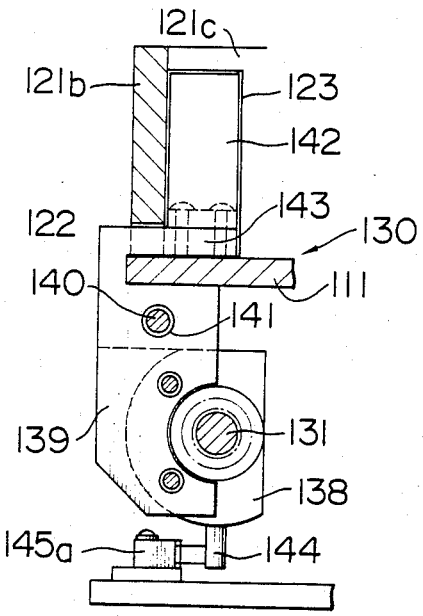
FIG. 13 is partial sectional view of the send out device taken along a line XIII—XIII in FIG. 12.

A slide piece 138 is threaded on the feed screw 131, and as shown in FIG. 13, a supporting member 139 is secured to one side of the slide piece 138 not to interfere with the slide piece 138. A guide rod 140 parallel with the feed screw 131 is provided at a position above the feed screw 131 as shown in FIG. 13. By inserting the rod 140 through an opening 141 of the supporting member 139, this supporting member 139 can move the slide piece 138 in the axial direction without rotating the same. Furthermore, the supporting member 139 supports a push plate 142 for sending out the sample.

More particularly, the supporting member 139 extends from the lower side to the front side of the supporting plate 111 and is formed with an arm 143 passing through an opening 122 across substantially the width of a side wall 121b at the lower end to overlie the supporting plate 111. The push plate 142 is secured to the upper surface of the push plate 142 having substantially the same or a little smaller width than the sample 112 so that the push plate 143 can move into and out of the magazine 120 in an opening 123 formed in another side wall 121c and along the inner surface of the side wall 121b. With this construction, as the feed screw 131 rotates a predetermined number of revolutions, the slide piece 138 is moved laterally by a distance corresponding to one sample, whereby the push plate 140 pushes the uppermost row of the samples from its righthand side as viewed in FIG. 11.

A projection 144 is provided for the lower portion of the slide piece 138 for actuating limit switches 145a and 145b (see FIG. 12) at the start and end positions. In FIG. 12, reference numeral 145a designates a bracket for supporting the bearing 132a, gear 133b and motor 134, while reference numeral 147 designates a bracket for supporting the bearing 132b.

Figure 14:
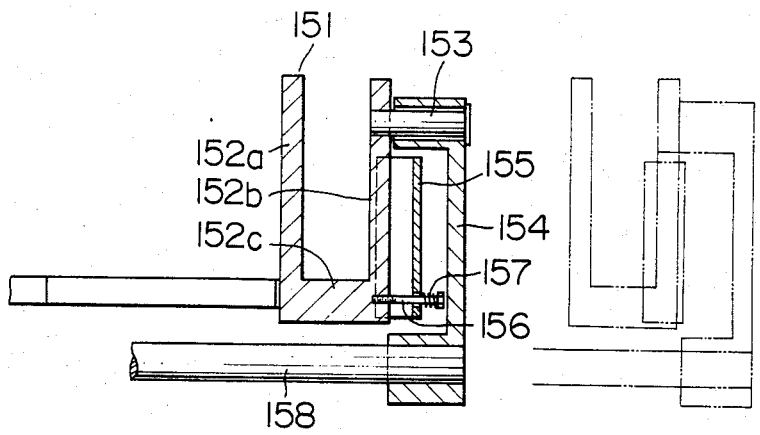
FIG. 14 is a fragmental sectional view showing a holder of a sample holding and conveying device.

By the intermittent lateral movement (to the left) of the uppermost row of the samples caused by the sample feed device 130, the leftmost sample 112 of the row is pushed out of the magazine 120 through a gate 124 provided through the side wall 121a of the magazine 120. The sample 112 thus pushed out is received in a receptacle 151 of a sample holding and conveying device 150. As shown in FIG. 14, the receptacle 151 takes the form of a letter U having two side walls 152a and 152b and a bottom wall 152c, two sides and the upper side of the receptacle 151 being opened. The receptacle 151 is swingably supported by a supporting member 154 by a horizontal pin 153 connected to the upper portion of the side wall 152b. The receptacle 151 further comprises a U shaped protective cover 155 which opens and closes opened sides of the receptacle. Since the purpose of the protective cover 155 is to prevent drop out of the sample from the receptacle its height may be a slightly longer than one half of the height of the receptacle and is secured thereto to be removable therefrom.

More particularly, the cover is secured to the bottom of the receptacle by a bolt 156 extending through the cover 155 and threaded into the bottom wall 152c. A coil spring 157 surrounding bolt 156 is interposed between the cover 155 and the head of the bolt 156 to urge the cover 155 to the closing state. When the cover 155 is pushed to the position shown in FIG. 14, the sides of the receptacle are opened.

One end of a supporting rod 158 is secured to the lower end of the supporting member 154 adapted to swingably support the receptacle 151, the supporting rod 158 extending beneath the receptacle 151 to the lower side of the supporting plate 111. As shown in FIG. 11, the receptacle supported by the supporting rod 158 in a manner just described is positioned in a recess formed at a sample receiving position in the front surface of the supporting plate 111 adjacent to the gate 124 of the magazine 120. Since the width of the recess of the supporting plate 111 for receiving the receptacle 151 is substantially equal to the lateral width of the U shaped holding member, both side edges of the protective cover 155 abut the opening of the recess. Thus the protective cover is moved away from the holding member to open its both opened sides while compressing the coil spring 157. The inner surface of the bottom wall 152c of the receptacle 151 is made to lie in the same level as the upper surface of the supporting plate 111 then the receptacle 151 is at the sample receiving position. The depth of the recess is determined such that its opening aligns with the gate 124 that is the leftside of the magazine 120. The supporting rod 158 extends beneath the supporting plate 111 along the side wall 121a of the magazine 120, in other words in the direction of columns as shown in FIGS. 11 and 12.

Figure 15:
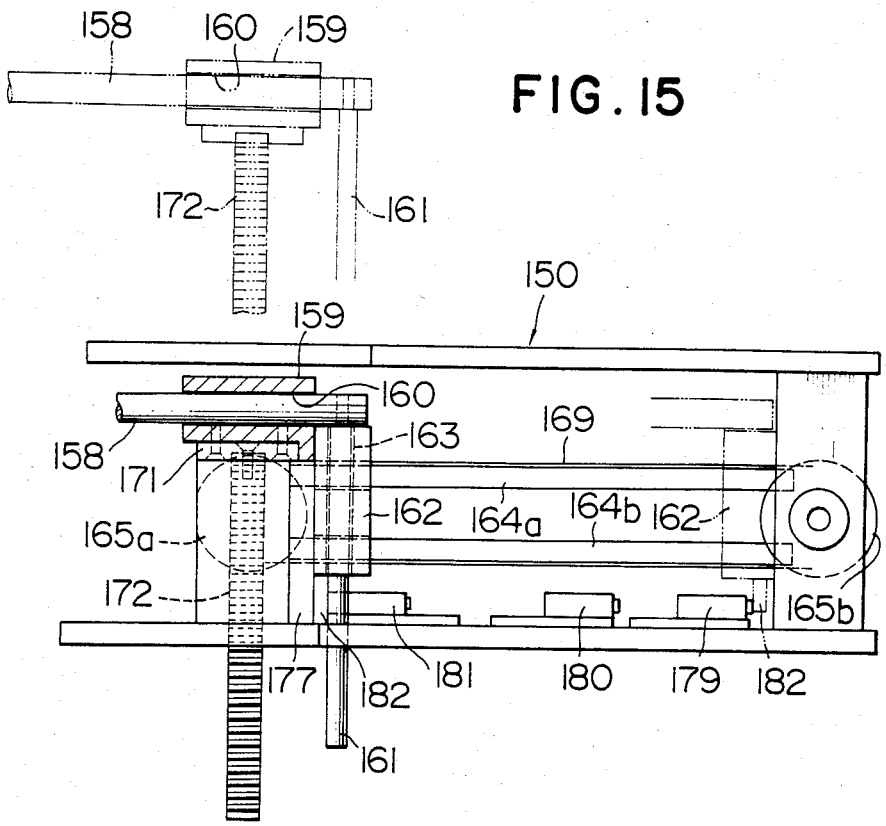
FIG. 15 is a diagrammatic side view showing the sample holding and conveying device taken along a line XV—XV in FIG. 12.

As shown in FIG. 15, the supporting rod 158 extends through an opening 160 of a guide member 159 and its outer end is connected to a vertical guide rod 161 movable in the vertical direction. The guide rod 161 passes through an opening 163 of a vertical bushing 162 slidably supported by a pair of parallel guide rods 164a and 164b parallel with the guide rod 158. Timing pulleys 165a and 165b are disposed near both ends of the guide rods 164a and 164b. The timing pulley 165a is driven by an electric motor 166, while the other timing pulley 165a is journaled by a bearing 168 supported by brackets 167a and 167b adapted to secure the ends of the guide rods 164a and 164b. The two timing pulleys 165a and 165b are coupled together by a belt 169 having a coarse inner surface. The upper run of the belt 169 is in contact with the bushing 163 so that as the motor 166 is rotated forwardly or reversely the bushing 162 is reciprocated along guide rods 164a and 164b with the result that supporting rod 158 connected to the guide rod 161 extending through the bushing 162 is also reciprocated in the vertical direction. Consequently, the receptacle 151 is reciprocated between the sample receiving position at the recess and a predetermined position in front of it.

The receptacle 151 is raised to a predetermined level for the purpose of inserting the aspirator of the blood diagnostic apparatus into the sample that is in the test tube.

The elevating device 170 of the receptacle 151 is constructed as follows. As has been described, the supporting rod 158 carrying the receptacle 151 is slidably supported by guide member 159. As shown in FIG. 15, a rack mounting plate 171 is secured to the lower surface of the guide member 159 and the upper end of a vertically extending rack 172 is secured to the lower surface of the rack mounting plate 171. As shown in FIG. 12 the rack 172 is slidable in a groove of a rack guide 173. As shown in FIG. 12, a gear 174b driven by an electric motor 175 through a gear 174a engages the rack 172. A projection 176 is provided for the gear 174a for actuating a limit switch 178 mounted on a bracket 177 supporting the motor 175. The bracket 177 not only rotatably supports the gear 174b but also supports the rack guide 172 and one ends of the pair of guide rods 164a and 164b.

Consequently, when the motor 175 is energized the gear 174b moves the rack 172 upwardly, for example, through gear 174a. Consequently, the guide member 159 is raised by the rack to raise the supporting rod 158. When the gear 174a is rotated one revolution, projection 176 actuates the limit switch 178 for stopping the motor 175. After a predetermined time, the motor 175 is reversed by a control signal from another control device, not shown, to lower the supporting rod 158. As the guide rod 161 can move freely through the bushing 162, supporting rod 158 can be moved in the vertical direction while being moved in the horizontal direction.

During the horizontal motion, the receptacle 151 passes through these positions, that is a position at which the sample is exchanged after pulling back the receptacle 151 to the magazine 120, a blood stirring position at a intermediate position between the sample exchanging position and the blood diagnostic apparatus, and the sample set position. Three limit switches 179, 180 and 181 are disposed along the guide rods 164a for controlling the motor 166 to stop the receptacle 151 at these three positions. A depending projection 182 for actuating these limit switches is secured to the bottom of the bushing 162.

When the receptacle 151 is returned to the sample exchanging position after finishing the diagnosis of one sample, it is returned to the lowermost row of the magazine by the sample feed device 190 through a return passage 191 to the left of the side wall 121a of the magazine 120. The side wall 121a is provided for one edge of an elongated rectangular opening 113 provided for the purpose of preventing collision of the guide member 159 supporting the holding rod 158 against the supporting plate 111, and another side wall 192 is provided for the other edge of the opening. The return passage 191 is defined between the side wall 192 and a side wall 193 mounted on the supporting plate 111. The front ends of the side wall 192 and the side wall 121a which define the return passage 191 terminate at the same position so as to form an inlet 194 opposing the gate 124 together with the recess of the supporting plate 111. The rear end of the return passage 191 is communicated with the lowermost row of the magazine 120 through a L shaped passage through a gate 125 and a outlet 195 formed between the lower ends of the side wall 121a and 192 and the lower edge 221 of the magazine.

When the receptacle 151 is returned to the sample exchanging position, the send out device 130 operates to actuate the push plate 142 to push one step the uppermost row of the samples toward gate 124 so that a new sample 112 is supplied into the receptacle, while at the same time, a sample which has been diagnosed is discharged from the receptacle 151. The sample thus discharged is moved into the fore or upper end of the return passage 191 through inlet 194. During the next reciprocating motion of the receptacle 151 the sample thus discharged is moved one step toward the lowermost row in the magazine by the first push out device 196.

Although not shown in the drawing, a photodetector is provided above the exchange position so as to check whether a test tube is contained in the sample or not when the sample holding and transfer device 150 reaches the sample exchange position. When the sample does not contain a test tube, it is skipped to the return passage 191 and returned to the lowermost row without advancing the sample holding and transferring device 150 to the stirring apparatus.

The first push out device 196 comprises a push out member 197 projecting into the return passage 191 through an opening 212 at the lower end of the side wall 193. Normally, the push out member 197 is held at a waiting position so as not to interfere with the downward movement of the diagnosed sample. The outer end of the push out member 197 is connected to an operating rod 198 extending along the side wall 193 and on the supporting plate 111, on the outside of the return passage. The other end of the operating rod 198 is pivotally connected to one end of an operating lever 199 pivotally connected to a pin 250 secured to the supporting plate 111. A roller 200 acting as a follower cam is provided at an intermediate point of the operating lever 199.

One end of the operating lever 204 of the second push out device 203 is also pivotally connected to the pin 250. The operating lever 204 extends rearwardly at an angle of about 90° with respect to the operating lever 199 and the other end of the lever is loosely connected to an operating rod 205. A follower roller 206 is also mounted at an intermediate point of the operating lever 204. A cam disc 207 is provided with its periphery contacted with both operating levers 199 and 204. A portion of the periphery of the disc 207 is cut away to form a linear cam portion 208.

When the periphery of the cam disc 207 except the linear cam portion engages the cam follower rollers 200 and 206, the angle between operating levers 199 and 204 is increased.

Consequently, the operating lever 199 of the first push out device 196 pushes the operating lever 198 forwardly (upwardly) for maintaining the push out member 197 at the waiting position. The operating rod 198 is biased by a coil spring 202 interposed between a guide bushing 201 slidably receiving the operating rod 198 and a flange 251 secured thereto. Accordingly, when the cam follower roller 200 engages the cam portion 208, the operating lever 199 is moved rearwardly by the force of coil spring 202, whereby the push out member 197 moves downwardly a sample 112 in the uppermost position of the return passage 191.

The operating rod 205 connected to the operating lever 204 extends into the return passage 191 in alignment with the lowermost row in the magazine. A push out member 209 is secured to the other end of the rod 205 for pushing a sample at the lower end of the return passage to a waiting position between an outlet 195 and a gate 125. This operating rod 205 too is biased to project into the return passage 191 by a coil spring 211 interposed between a guide bushing 210 and a flange 252 secured to the operating rod 205. When the cam follower roller 206 engages the periphery of the cam disc 207 except the linear portion 208, push out member 209 of the operating rod 205 is received in the opening 212 of the side wall 193 so as not to project into the return passage 191.

Accordingly, when the linear portion 208 engages the cam follower roller 206 as a result of the rotation of the cam disc 207, the operating lever 205 is moved to the right by the force of the coil spring to project the push member 209 into the return passage 191.

The cam disc 207 is rotated by an electric motor, not shown, secured to the lower side of the supporting plate 111, and rotates one revolution intermittently. Such rotation is controlled by actuating a limit switch 214 disposed on one side of the cam disc 207 by a projection 213 secured to the lower surface of the cam disc 207.

As above described, when the diagnosed samples 112 are sequentially pushed out into the return passage and moved downwardly, one after one, by the first push out device 191, the uppermost row of the magazine would become vacant when the last sample of that row is transferred to the receptacle 151. Then the next row in the magazine is raised by a shifting device 220 to be described later, whereby the lowermost row becomes vacant. Since the number of samples accommodatable in the return passage 191 is made to be equal to the number of samples in each row (in this example, 10) while the last sample of the uppermost row is received in the receptacle 151 and reciprocated for diagnosis, and when the samples in the return passage 191 are moved downwardly by one step, the first sample of the uppermost row would come to engage the side wall 121d at the lower end of the return passage 191.

Consequently, as the first sample of the second row (now in the uppermost position) is mounted on the receptacle 151 by the first push out device 130, the rotation of the cam disc 207 is commenced, and at first its cam portion 208 engages the roller 206 of the operating lever 204 so that this lever 204 is rotated in the counterclockwise direction so as to push the sample at the lowermost position in the return passage to the waiting position between the inlet 195 and the gate 125. As the rotation of the cam lever 207 continues, the operating levers 204 and 199 are rotated in the clockwise direction. As a consequence, samples in the return passage 191 are moved downwardly to make vacant the uppermost end of the return passage 191 for receiving the sample under diagnosis.

The shift device 220 comprises a push plate 221 integrally connected to the lower side wall 121d of the magazine 120. The push plate 221 has a length substantially equal to the length of one row in the magazine 120. A mounting member 222 secured to the central portion of the push plate 221 is connected to a slide piece 224 projecting from an opening 233 formed through the supporting plate 111.

As shown in FIG. 12, the slide piece 224 is slidably supported by two parallel guide rods 226a and 226b secured to a bracket 225 and extending in the column direction of the magazine 120. One end of a connecting lever 227 is pivotally connected to one side of the slide piece 224, while the other end of the lever 227 is connected to an eccentric pin 255 of a circular disc 229 driven by an electric motor 228 so that as the disc 229 rotates one revolution, the slide disc 224 is reciprocated once. Consequently, the push plate 221 connected to the slide piece 224 pushes upwardly the lowermost row of the samples and then returns to the original position. The stroke of the push plate 221 is equal to the width of one row and the stroke can readily be varied by changing the position of the pin 255 on the disc 229.

The automatic sample feed apparatus 110 described above operates as follows.

100 samples 112 are disposed in the magazine 120 in a matrix comprising 10 columns and 10 rows. Then the send out device 130 operates to move towards left the uppermost row by one step (equal to the size of a sample) by push plate 142 so as to mount the leftmost sample on the receptacle 151.

Then the motor 166 of the sample holding and transfer device 150 is actuated to move the slide piece 162 along guide rods 164a and 164b to advance the receptacle 151 toward the blood diagnostic apparatus. Then the projection 182 at the lower end of the slide piece 162 actuates limit switch 180 to stop motor 166. At this time, the receptacle 151 is brought to a position below two rollers 231a and 231b of the stirring apparatus 130 with the top of the test tube positioned between these rollers without contacting them.

Then the stirring apparatus 230 stires blood in the test tube. The stirring apparatus 230 shown in FIG. 11 comprises a gear train 232 for rotating the rollers 231a and 231b in the opposite directions, a belt and crank mechanism to drive one roller 231a and to move in unison two rollers 231a and 231b to the left and right. Consequently, the top of the test tube is swung about the pivot shaft 153 of the receptacle 151 by being alternately contacted by rollers 231a and 231b. In the same manner as the stirring apparatus shown in FIGS. 1–3, the test tube is rotated alternately in the opposite directions by the frictional contact of the oppositely rotating rollers 231a and 231b for stirring the blood to a homogeneously suspended state. By a mechanism similar to that shown in FIGS. 1–3 the stirring apparatus is stopped after a predetermined time. At this time the head of the test tube is stopped on the line of movement of the receptacle 151.

Thereafter, the receptacle 151 is advanced to the test tube set position of the blood diagnostic apparatus by the motor 166 and held at that position by limit switch 181. Then motor 175 is operated to raise rack 172 through gears 174a and 174b, whereby the supporting rod 158 slidably supported by guide piece 159 is raised to a predetermined height. Then the aspirator is inserted into the test tube to suck all or a portion of the blood contained therein.

Then the rotation of the motor 175 is reversed to lower the receptacle 151 and the rotation of motor 166 is also reversed to return the receptacle to the sample exchange position at which its projection 182 at the lower end of the slide piece 162 actuates limit switch 179 to stop motor 166. The send out device 130 is operated again to move one step to the left the uppermost row in the magazine 120, whereby diagnosed sample in the receptacle is pushed out into the return passage 191 by the feed device 190.

Thus, when all samples of the uppermost row have been sent out from the magazine, the remaining rows are raised to make vacant the lowermost row into which samples in the return passage 191 are sequentially sent each time the receptacle is reciprocated by the sample holding and transfer device 150 while the samples of the second row (now in the uppermost position) are sequentially supplied to the receptacle. When all samples in the magazine have been diagnosed the automatic sample feed apparatus is stopped. At this time, 100 samples are disposed in a matrix in the magazine, but the order of samples in each row is reversed. For example, at the time of starting shown in FIG. 11, the leftmost sample of the uppermost row is No. 1, but after completion the diagnosis of all samples, this No. 1 sample is brought to the rightmost position. For the purpose of making easy confirmation of this state the holder of No. 1 sample may be colored black, for example. Further, when all or some of the test tubes of one row does not contain blood, the holders of such test tubes are colored.

Figure 16:
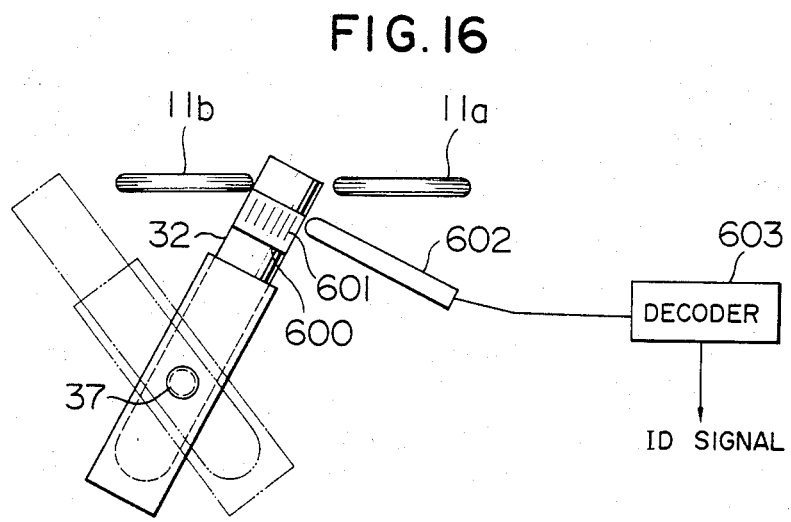
FIG. 16 is a diagrammatic representation of an identification code detector associated with the stirring apparatus shown in FIG. 1.

As above described according to the automatic sample feed apparatus, a number of samples are always arranged in a matrix in the magazine, so that storage and transfer of samples to other diagnostic apparatus can be made rapidly. Moreover as the samples are circulated, one after one, supply and withdrawal of the samples to and from the stirring apparatus and the blood diagnostic apparatus can be made rapidly and automatically.

Where there are a large number of sampled bloods it is advantageous to use an identification code detector as shown in FIG. 16. Thus, an identification code (ID) label 600 is boned near the top of the test tube 32. The label is printed with an identification code 601. In this example, the code is made up of a plurality of parallel stripes of different width. By properly combining the stripes, a number of identification codes can be prepared. Adjacent the ID label 600 is positioned a code detector 602 which reads the code with a photosensor, a phototransistor, for example. The output of the code decoder 602 is decoded by a decoder 603 into a digital ID signal utilized to identify a person to be diagnosed. Since such identification codes and code detector are used in many industrial field, for example in a tool magazine in a machining center, detailed description thereof is believed unnecessary.

Although in the foregoing description control circuits for various motors are not shown, it is clear that the motors can be operated by a well known sequence controller. Further, it will be clear that electric motors can be substituted by such other drive means as hydraulic or pneumatic drive means. The automatic operation can be made with a commercial microcomputer.

What is claimed is:

1. Apparatus for stirring material contained in a test tube having a longitudinal axis and upper and lower ends, comprising:
   a holder for supporting said test tube;
   means for swingably supporting said holder;
   two spaced rollers rotating in opposite directions about respective roller axes; and
   reciprocating means for causing relative movement between said test tube and said rollers such that said rollers alternately engage said upper end of said test tube to alternately rotate said test tube in opposite directions about said longitudinal axis.

2. The stirring apparatus according to claim 1 wherein said two rollers are disposed in the same plane so as to cause said test tube to swing in the plane of said axes of said rollers.

3. The stirring apparatus according to claim 1 wherein said means for swingably supporting said holder has a pivot pin positioned at a point above one half of the length of said test tube.

4. The stirring apparatus according to claim 1 wherein said material contained in said test tube is blood.

5. Automatic sample feed apparatus for feeding samples to a stirring apparatus, comprising:
- a plurality of samples, each sample comprising a test tube for containing a material to be stirred and a holder for said test tube;
- a magazine in which said plurality of samples are aligned in a matrix of a plurality of rows and a plurality of columns;
- a send out device for intermittently moving the samples of a foremost row of said matrix by a distance corresponding to a dimension of one sample such that an individual sample is intermittently sent out from said magazine;
- sample holding and transfer means for receiving said individual sample sent out from said magazine;
- means for reciprocating said sample holding and transfer means toward and away from said stirring apparatus;
- returning means for moving said sample from said sample holding and transfer means to a rearmost row in said magazine; and
- means for moving forwardly all rows remaining in said magazine by a distance equal to a dimension of one row when all samples of said foremost row have been sent out of said magazine.

6. The automatic sample feed apparatus according to claim 5, further comprising a receptacle for holding one of said samples, a supporting rod for supporting said receptacle, and means for reciprocating said supporting rod toward and away from said magazine.

7. The automatic sample feed apparatus according to claim 6, further comprising elevator means which moves said rod in the vertical direction for adjusting vertical position of said receptacle.

8. The automatic sample feed apparatus according to claim 6 wherein said receptacle takes the form of a letter U with opposed sides open for receiving and discharging a sample, and said sample holding and transfer apparatus further comprises a protective cover for said receptacle, and means for reciprocating said protective cover toward and away from said receptacle for closing and opening said open opposed sides of said receptacle.

9. The automatic sample feed apparatus according to claim 5 wherein said returning means comprising a return passage for returning samples from said sample holding and transfer means to said rearmost row in said magazine, a first push out means for moving said samples through said return passage and a second push out means for pushing said samples from said return passage into a vacant row formed when said remaining rows are pushed toward the foremost row.

10. Automatic sample feed and stirring apparatus comprising:
- a plurality of samples, each sample comprising a test tube for containing material to be stirred and having a longitudinal axis and a holder for said test tube;
- a magazine in which said plurality of samples are aligned in a matrix of a plurality of rows and a plurality of columns;
- a send out device for intermittently moving the samples of a foremost row of said matrix by a distance corresponding to a dimension of one sample such that an individual sample is intermittently sent out from said magazine;
- sample holding and transfer means for receiving and swingably supporting said individual sample sent out from said magazine;
- stirring means for simultaneously swinging said test tube and rotating said test tube in alternate opposite direction about said longitudinal axis of said test tube;
- means for reciprocating said sample holding and transfer means toward and away from said stirring apparatus;
- returning means for moving said sample from said sample holding and transfer means to a rearmost row in said magazine; and
- means for moving forwardly all rows remaining in said magazine by a distance equal to a dimension of one row when all samples of said foremost row have been sent out of said magazine.

* * * * *